United States Patent
Kennedy

(10) Patent No.: US 10,912,854 B1
(45) Date of Patent: Feb. 9, 2021

(54) RELIGHTABLE INCENSE PRODUCT AND PRODUCTION METHOD

(71) Applicant: Eugene Kennedy, Copeland, FL (US)

(72) Inventor: Eugene Kennedy, Copeland, FL (US)

( * ) Notice: Subject to any disclaimer, the term of this patent is extended or adjusted under 35 U.S.C. 154(b) by 2 days.

(21) Appl. No.: 16/149,982

(22) Filed: Oct. 2, 2018

Related U.S. Application Data

(60) Provisional application No. 62/566,614, filed on Oct. 2, 2017.

(51) Int. Cl.
| | | |
|---|---|---|
| *C11B 9/00* | (2006.01) | |
| *A61K 8/00* | (2006.01) | |
| *A61L 9/013* | (2006.01) | |
| *A61L 9/02* | (2006.01) | |

(52) U.S. Cl.
CPC .............. *A61L 9/013* (2013.01); *A61L 9/02* (2013.01); *C11B 9/00* (2013.01)

(58) Field of Classification Search
CPC .. C11B 9/00; C11B 9/02; A61Q 13/00; A61K 8/00; A61K 8/18
USPC ........................................................ 512/5, 1
See application file for complete search history.

(56) References Cited

FOREIGN PATENT DOCUMENTS

| | | | |
|---|---|---|---|
| CN | 102302793 | * | 8/2013 |
| RO | 112741 B1 | * | 12/1997 |
| TW | 215413 | * | 9/1992 |

OTHER PUBLICATIONS

Wu, TW 215413 Machine Translation, Sep. 22, 1992 (Year: 1992).*
Tesu et al, RO 112741 Machine Translation, Dec. 30, 1997 (Year: 1997).*
She, CN 1023027936 Machine Translation, Aug. 7, 2013 (Year: 2013).*

* cited by examiner

*Primary Examiner* — Jessica Whiteley
(74) *Attorney, Agent, or Firm* — John Rizvi; John Rizvi, P.A.—The Patent Professor®

(57) ABSTRACT

An incense product and production method thereof. The method may include mixing various incense components together to form a mixture, placing the mixture into an agitator, heating the mixture to form a heated mixture, placing the heated mixture into a tray and allowing the heated mixture to cool to form a cooled mixture, grinding the cooled mixture to a ground mixture, mixing a second set of non-heated plant material in with the ground mixture to form a final mixture, and pressing the final mixture to form a tablet.

15 Claims, 1 Drawing Sheet

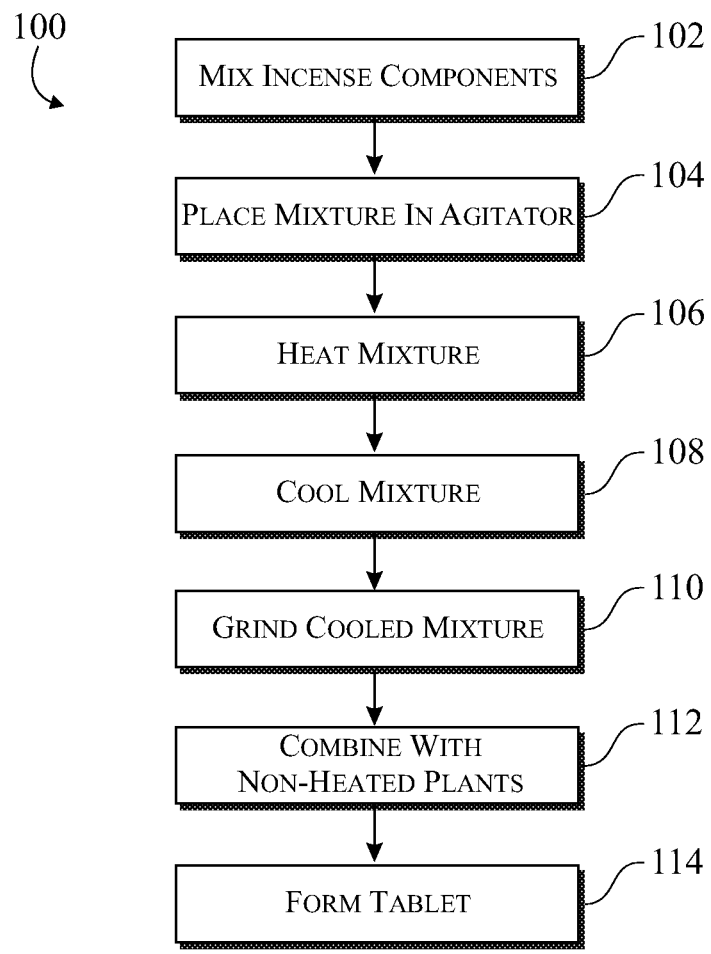

RELIGHTABLE INCENSE PRODUCT AND PRODUCTION METHOD

CROSS-REFERENCE TO RELATED APPLICATION

This application claims the benefit of U.S. Provisional Patent Application Ser. No. 62/566,614, filed Oct. 2, 2017, which is incorporated herein in its entirety.

FIELD OF THE INVENTION

The present invention generally relates to incense products and more particularly to a relightable incense product and production method thereof.

BACKGROUND OF THE INVENTION

Incense is an aromatic material which releases fragrant smoke when burned.

It is common for incense to be burned in various situations. For example, incense may be burned to release a pleasant or therapeutic aroma. Incense may also be burned as part of a ceremony or religious event.

However, currently available incense products have an inconvenient and troublesome limitation in that they are difficult to relight after being extinguished. This limitation is a problem in religious ceremonies where incense is required to be extinguished and relit multiple times.

Accordingly, there exists a need for an incense product that may be easily extinguished and relit.

SUMMARY OF THE INVENTION

Disclosed is an incense product configured to be easily lit and relit and configured to burn slowly, the incense product comprising, one or more of fir tree, paraffin, charcoal, sawdust, pine tree, basil, garlic, and myrrh.

Further disclosed is a method for producing an incense product, the method comprising, mixing various incense components together to form a mixture, placing the mixture into an agitator, heating the mixture at a temperature between 250 and 360 degrees Fahrenheit to form a heated mixture, placing the heated mixture into a tray and allowing the heated mixture to cool to form a cooled mixture, grinding the cooled mixture to a ground mixture, and pressing the ground mixture to form a tablet.

In another aspect, the tablet is configured to light quickly in 10-15 seconds.

In another aspect, the tablet includes one or more of: fir resin incense (melted), paraffin (melted), charcoal (powder), sawdust (powder), pine tree grinds (dried green grinds), basil (dried green grinds or oil), cannabis (dried green grinds or oil), garlic (dry powder), and myrrh (ground).

In another aspect, the fir resin is configured to homogenize the mixture, and for being burned to release a pleasant, calming smell and smoke.

In another aspect, the paraffin is configured to homogenize the mixture and cause the components to burn slowly.

In another aspect, the charcoal is configured to aid in burning the tablet while prolonging combustion.

In another aspect, the sawdust is configured to homogenize the mixture and cause slow burning carbonization.

In another aspect, the pine tree grinds is configured to provide a pleasant, clean, and pungent odor.

In another aspect, at least one of the basil and cannabis is configured to release a fresh smell.

In another aspect, the garlic is included to provide a harsh, dry, odor.

In another aspect, the myrrh has a strong odor to provide a strong scent to the tablet.

In another aspect, mixing the components includes: mixing fir resin, paraffin, charcoal, and sawdust together to a first mixture.

In another aspect, heating the mixture includes heating the mixture for a heating time between 15-25 minutes sufficiently for all the components to become homogenized to a homogenized mixture.

In another aspect, grinding the cooled mixture includes grinding the cooled mixture to a powder.

In another aspect, the pine tree grinds, basil, cannabis, garlic, and myrrh are fresh plants.

In another aspect, the method further comprises, mixing the fresh plants together to form mixed fresh plants (second mixture) and mixing the mixed fresh plants with the homogenized mixture.

In another aspect, the method further comprises refrigerating the fresh plants as refrigerated fresh plants.

In another aspect, the method further comprises grinding the fresh plants to a second mixture for being mixed with the homogenized mixture.

In another aspect, mixing the fresh plants with the homogenized mixture includes placing the fresh plants in an agitator with the homogenized mixture for being mixed with the homogenized mixture in the agitator to form a final mixture.

In another aspect, pressing the ground mixture includes placing the final mixture in a press, and pressing the final mixture in the press to form the tablet.

In another aspect, the method further comprises pressing the final mixture to a pressed final mixture.

In another aspect, the components are organic.

In another aspect, 25% of the tablet is fir resin incense, 0.8% is paraffin, 12% is charcoal, 20% is sawdust, 10% is pine tree grinds, 15% is basil and/or cannabis (e.g. oil), 0.1% is garlic, and/or 0.9% is myrrh.

In another aspect, the method further comprises, placing the first mixture in an agitator and concurrently agitating and heating the first mixture in the agitator.

In another aspect, the tablet is formulated to be lit while the tablet is held between a user's fingers such that the tablet does not burn the user's finger.

In another aspect, the first mixture is heated to be melted and homogenized in at least one of an oven and a heated agitator.

In another aspect, the first mixture is homogenized with heat and the second mixture includes non-heated plants, where the final mixture includes non-heated plant material.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which:

FIG. 1 schematically shows a method of producing an incense tablet, in accordance with aspects of the present disclosure.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Disclosed is an incense product configured to be easily lit and relit and configured to burn slowly. The incense product may comprise, one or more of fir tree, paraffin, charcoal, sawdust, pine tree, basil, garlic, and myrrh.

The illustration of FIG. 1 shows a method 100 for producing an incense product, the method comprising, at step 102 mixing various incense components together, as described in more detail below to form a mixture, at step 104 placing the mixture into an agitator, at step 106 heating the mixture at a temperature between 250 and 360 degrees Fahrenheit to form a heated mixture, at step 108 placing the heated mixture into a tray and allowing the heated mixture to cool to form a cooled mixture, at step 110 grinding the cooled mixture to a ground mixture, at step 112 mixing a second set of non-heated plant material in with the ground mixture to form a final mixture, and at step 114 pressing the final mixture to form a tablet. The steps in method 100 may be executed in the order shown in FIG. 1, as described herein, or in any appropriate order.

As such, the method may produce a tablet that is configured to light quickly, or approximately, in 10-15 seconds. "Approximately" may refer to a given value in a range of plus or minus 10 seconds or may refer to a given value in a range of plus or minus 20%. The tablet may include one or more of the following components: fir resin incense (melted), paraffin (melted), charcoal (powder), sawdust (powder), pine tree grinds (dried green grinds), basil (dried green grinds or oil), cannabis (dried green grinds or oil), garlic (dry powder), and myrrh (ground). The fir resin may be included, selected, or configured to homogenize the mixture, and for being burned to release a pleasant, calming smell and smoke. The paraffin may be included, selected, or configured to homogenize the mixture and cause or allow the components to burn slowly. The charcoal may be included, selected, or configured to aid in burning the tablet while prolonging combustion of the tablet. The sawdust may be included, selected, or configured to homogenize the mixture and cause slow burning carbonization of the tablet. The pine tree grinds may be included, selected, or configured to provide a pleasant, clean, and pungent odor when the tablet is used. At least one of the basil and cannabis may be included, selected, or configured to release a fresh smell when the tablet is used. The garlic may be included to provide a harsh, dry, odor. The myrrh may be included, selected, or configured to have a strong odor to provide a strong scent to the tablet.

In one example, the pine tree grinds, basil, cannabis, garlic, and myrrh are fresh plants. In one example, exactly or approximately 25% of the produced tablet is fir resin incense, 0.8% is paraffin, 12% is charcoal, 20% is sawdust, 10% is pine tree grinds, 15% is basil and/or cannabis (e.g. oil), 0.1% is garlic, and/or 0.9% is myrrh.

At step 102, mixing the components may include: mixing fir resin, paraffin, charcoal, and sawdust together to a first mixture.

The method may further comprise, at step 104 and/or step 106, placing the first mixture in an agitator and concurrently agitating and heating the first mixture in the agitator. At step 104 and/or step 106, the first mixture may be heated to be melted and homogenized in at least one of an oven and a heated agitator. At step 106, heating the mixture may include heating the mixture for a heating time between 15-25 minutes sufficiently for all the components to become homogenized to a homogenized mixture.

At step 110, grinding the cooled mixture may include grinding the cooled mixture to a powder.

The method may further comprise, at step 112, mixing the fresh plants together to form mixed fresh plants (second mixture) and mixing the mixed fresh plants with the homogenized mixture. The method may also include refrigerating the fresh plants as refrigerated fresh plants before mixing the fresh plants with one another (second mixture) or mixing the fresh plants with the homogenized mixture to form a final mixture. The method may further comprise, at step 112, grinding the fresh plants to a second mixture for being mixed with the homogenized mixture. At step 112, mixing the fresh plants with the homogenized mixture may include placing the fresh plants in an agitator with the homogenized mixture for being mixed with the homogenized mixture in the agitator to form a final mixture.

At step 114, pressing the ground mixture may include placing the final mixture in a press, and pressing the final mixture in the press to form the tablet. Therefore, the final mixture may be pressed to a pressed final mixture.

As such, the produced tablet is formulated to be lit while the tablet is held between a user's fingers such that the tablet does not burn the user's finger. The tablet is able to be lit and re-lit one or more times. Further, the first mixture may be homogenized with heat and the second mixture may include non-heated plants, such that the final mixture and subsequently the tablet includes non-heated plant material. It is to be understood that one or more, or all of the herein described components may be organic.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A method for producing an incense product, the method comprising:
    mixing various incense components together to form a mixture;
    placing the mixture into an agitator;
    heating the mixture at a temperature between 250 and 360 degrees Fahrenheit to form a heated mixture;
    placing the heated mixture into a tray;
    allowing the heated mixture to cool to form a cooled mixture;
    grinding the cooled mixture to a ground mixture; and
    and pressing the ground mixture to form a tablet;
    wherein mixing the incense components includes: mixing fir resin, paraffin, charcoal, and sawdust together to a first mixture; and
    wherein approximately 25% of the incense product is fir, approximately 0.8% is paraffin, approximately 12% is charcoal, approximately 20% is sawdust, approximately 10% is pine, approximately 15% is basil and/or cannabis, approximately 0.1% is garlic, and approximately 0.9% is myrrh.

2. The method of claim 1, wherein heating the mixture includes heating the mixture for a heating time between 15-25 minutes sufficiently for all the components to become homogenized to a homogenized mixture.

3. The method of claim 1, wherein grinding the cooled mixture includes grinding the cooled mixture to a powder.

4. The method of claim 2, wherein the method further comprises, mixing fresh plants together to form a second mixture and mixing the second mixture with the homogenized mixture.

5. The method of claim 4, wherein the method further comprises refrigerating the fresh plants before forming the second mixture.

6. The method of claim 4, wherein the method further comprises grinding the fresh plants.

7. The method of claim 4, wherein mixing the second mixture with the homogenized mixture includes placing the fresh plants in an agitator with the homogenized mixture for being mixed with the homogenized mixture in the agitator to form a final mixture.

8. The method of claim 7, wherein pressing the ground mixture includes placing the final mixture in a press, and pressing the final mixture in the press to form the tablet.

9. The method of claim 1, wherein the method further comprises, placing the first mixture in an agitator and concurrently agitating and heating the first mixture in the agitator.

10. The method of claim 1, wherein the first mixture is heated to be melted and homogenized in at least one of an oven and a heated agitator.

11. The method of claim 7, wherein the first mixture is homogenized with heat and the second mixture includes non-heated plants, where the final mixture includes non-heated plant material.

12. The method of claim 4, wherein pine, basil, cannabis, garlic, and myrrh are included in the fresh plants.

13. The method of claim 1, wherein the components are organic.

14. The method of claim 1, wherein as components to form the incense product, the fir is a resin, the paraffin is melted, the charcoal is a powder, the sawdust is a powder, the pine is dried grinds, the basil is at least one of dried grinds and an oil, the cannabis is at least one of dried grinds and an oil, the garlic is a dry powder, and the myrrh is ground.

15. The method of claim 1, wherein the tablet is configured to light in approximately 10-15 seconds.

* * * * *